US006730789B1

(12) United States Patent
Birault et al.

(10) Patent No.: US 6,730,789 B1
(45) Date of Patent: May 4, 2004

(54) COMPOSITION FOR DYEING KERATINOUS FIBERS CONTAINING 3 AMINO PYRAZOLO- [1,5-A] PYRIDINES, DYEING METHOD, NOVEL 3-AMINO PYRAZOLO-[1, 5-A] PYRIDINES

(75) Inventors: Véronique Birault, Saffron Walden (GB); Madeleine Leduc, Paris (FR); Eric Terranova, Magagnosc (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 10/130,535

(22) PCT Filed: Oct. 18, 2000

(86) PCT No.: PCT/FR00/02903

§ 371 (c)(1),
(2), (4) Date: Dec. 17, 2002

(87) PCT Pub. No.: WO01/35917

PCT Pub. Date: May 25, 2001

(30) Foreign Application Priority Data

Nov. 19, 1999 (FR) .............................. 99 14582

(51) Int. Cl.$^7$ .......................................... C07D 217/06
(52) U.S. Cl. ..................................... 546/121
(58) Field of Search ......................... 546/121

(56) References Cited

U.S. PATENT DOCUMENTS

| | | | |
|---|---|---|---|
| 3,536,436 A | | 10/1970 | Lange |
| 4,003,699 A | | 1/1977 | Rose et al. |
| 4,322,212 A | | 3/1982 | Konrad et al. |
| 4,823,985 A | | 4/1989 | Grollier et al. |
| 5,061,289 A | | 10/1991 | Clausen et al. |
| 5,102,878 A | * | 4/1992 | Shiokawa et al. ..... 514/217.07 |
| 5,179,103 A | * | 1/1993 | Shiokawa et al. .......... 514/300 |
| 5,234,818 A | * | 8/1993 | Zimmermann et al. ....... 435/28 |
| 5,296,490 A | * | 3/1994 | Shiokawa et al. .......... 514/300 |
| 5,334,505 A | * | 8/1994 | Zimmermann et al. ....... 435/18 |
| 5,338,743 A | * | 8/1994 | Shiokawa et al. .......... 514/300 |
| 5,380,340 A | | 1/1995 | Neunhoeffer et al. |
| 5,457,200 A | * | 10/1995 | Zimmermann et al. ..... 544/281 |
| 5,525,480 A | * | 6/1996 | Zimmermann et al. ....... 435/18 |
| 5,766,576 A | | 6/1998 | Löwe et al. |
| 5,980,585 A | | 11/1999 | Terranova et al. |
| 6,027,538 A | | 2/2000 | Vandenbossche et al. |
| 6,099,592 A | | 8/2000 | Vidal et al. |
| 6,099,593 A | | 8/2000 | Terranova et al. |
| 6,248,137 B1 | | 6/2001 | Terranova et al. |

FOREIGN PATENT DOCUMENTS

| | | |
|---|---|---|
| DE | 23 59 399 | 6/1975 |
| DE | 38 43 892 | 6/1990 |
| DE | 41 33 957 | 4/1993 |
| DE | 195 43 988 | 5/1997 |
| EP | 0 030 680 | 6/1981 |
| EP | 0 299 209 | 1/1989 |
| EP | 0 433 855 | 6/1991 |
| EP | 0 770 375 | 5/1997 |
| EP | 0 904 769 | 3/1999 |
| FR | 2 586 913 | 3/1987 |
| FR | 2 733 749 | 11/1996 |
| FR | 2 750 048 | 12/1997 |
| FR | 2 771 631 | 6/1999 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 96/15765 | 5/1996 |

OTHER PUBLICATIONS

English language Derwent Abstract of EP 0 770 375, May 2, 1997.

English language Derwent Abstract of JP 2–19576, Jan. 23, 1990.

English language Derwent Abstract of JP 5–163124, Jun. 29, 1993.

K. T. Potts et al., "Bridgehead Nitrogen Heterocycles. I. A Convenient Synthesis of Pyrazolo[1,5–a]pyridines," The Journal of Organic Chemistry, vol. 33, No. 10, Oct. 1968, pp. 3766–3770.

M. Hirobe et al., "Syntheses of Novel Antimicrobial Compounds: Pyazolo [5, 1–b] thiazole, Imidazo [1,2–b]pyrazole, and Thiazolo [3,2–b] dihydro–1,2–diazepine," Chemical & Pharmaceutical Bulletin, vol. 22, No. 2, Feb. 1974, pp. 482–484.

Y. Tumura et al., "A Novel Method For Heteroaromatic N–Imines," Tetrahedron Letters, No. 40, 1972, pp 4133–4135.

Y. Tamura et al., "O–Mesitylenesulfonylhydroxylamine and Related Compounds—Powerful Aminating Reagents," International Journal of Methods in Synthetic Organic Chemistry, No. 1, Jan. 1977, pp. 1–17.

Hisao Ochi et al., "Studies of Heterocyclic Compounds. VIII. Synthesis and Tautomerism of 2–Hydroxypyrazolo [1, 5–a]pyridine," Bulletin of the Chemical Society of Japan, vol. 49, No. 7, 1996, pp. 1980–1984.

Roland Krischke et al., "Pyridinium–N–imid als additionsbereites Azomethinimin," Liebigs Ann. Chem., vol. 1977, No. 3, Mar. 1977, pp. 498–505.

Rolf Huisgen et al., "1.3–Additionen Mit Pyridin–Imin, Chinolin–Imin, Isochinolin–Imin Und Phenanthridin–Imin," Tetrahedron Letters, No. 9, May 1962, pp. 387–391.

(List continued on next page.)

*Primary Examiner*—D. Margaret Seaman
(74) *Attorney, Agent, or Firm*—Finnegan, Henderson, Farabow, Garrett & Dunner, L.L.P.

(57) ABSTRACT

The invention concerns novel oxidative composition for dyeing keratinous fibres comprising at least a 3-amino-pyrazolo-[1,5-a]-pyridine of Formula (I), the dyeing method using said composition, novel 3-amino pyrazolo-[1,5-a]-pyridines, and the method for preparing them.

24 Claims, No Drawings

OTHER PUBLICATIONS

Paul L. Anderson et al., "1,3–Dipolar Addition of Pyridine N–Imine to Acetylenes and the Use of C–13 NMR in Serveral Structural Assignments," Journal of Heterocyclic Chemistry, vol. 18, No. 6, Oct. 1981, pp. 1149–1152.

Ling–Ching Chen et al., "Synthesis and 1,3–Dipolar Cycloaddition of 3–Hydroxy –5– Methoxy–Pyridinium N–Imine," Heterocycles, vol. 24, No. 12, Dec. 1986, pp. 3411–3415.

Peter Gmeiner et al., "Dopamine Autoreceptor Agonists: Computational Studies, Synthesis and Biological Investigations," Bioorganic & Medicinal Chemistry Letters, vol. 3, No. 8, 1993, pp. 1477–1483.

Brian Maurice Lynch et al., "Condensed Pyrazoles. 1. Nitro and Nitroso Derivatives of Pyrazolo [1,5–a] pyridine," Journal of Heterocyclic Chemistry, vol. 11, No. 2, Apr. 1974, pp. 223–225.

Yasumitsu Tamura et al. "New Routes to the v–Triazolo[1, 5–a]pyridine and Pyrazolo[1,5–a]pyridine Ring Systems," Journal of Heterocyclic Chemistry, vol. XII, Jun. 1975, pp. 481–483.

Seigo Suzue et al., "Synthetic Antimicrobials. II. Synthesis of Pyrozolo[1,5a]pyridine Derivalves, (1)," Chemical & Pharmaceutical Bulletin, vol. 21, No. 10, 1973, pp. 2146–2160.

* cited by examiner

COMPOSITION FOR DYEING KERATINOUS FIBERS CONTAINING 3 AMINO PYRAZOLO- [1,5-A] PYRIDINES, DYEING METHOD, NOVEL 3-AMINO PYRAZOLO-[1, 5-A] PYRIDINES

The invention relates to novel compositions for the oxidation dyeing of keratinous fibers, comprising at least one 3-aminopyrazolo[1,5-a]pyridine as oxidation base, to the dyeing method employing this composition, to novel 3-aminopyrazolo[1,5-a]pyridines, and to their use for the oxidation dyeing of keratinous fibers.

It is known to dye keratinous fibers and particularly human hair with dyeing compositions comprising oxidation dye precursors, in particular ortho- or para-phenylenediamines, ortho- or para-aminophenols, and heterocyclic compounds such as diaminopyrazole derivatives, which are referred to generally as oxidation bases. The oxidation dye precursors or oxidation bases are colorless or virtually colorless compounds which, when combined with oxidizing products, are able to give rise to colored compounds and dyes by a process of oxidative condensation. A common feature of these compounds is possession of an amino group and a hydroxyl group or of two amino groups, this giving them their character as oxidation bases.

It is also known that the shades obtained with these oxidation bases can be varied by combining them with couplers or coloration modifiers, the latter being selected in particular from aromatic meta-diamines, meta-aminophenols, meta-diphenols, and certain heterocyclic compounds.

The variety of molecules employed as oxidation bases and couplers makes it possible for a rich palette of colors to be obtained.

The "permanent" coloration obtained by means of these oxidation dyes is required, moreover, to meet a certain number of requirements. Hence it must have no toxicological drawbacks, it must allow shades of the desired intensity to be obtained, and it must exhibit good stability via a vis external agents (light, inclement weather, washing, perming, perspiration, and friction).

The dyes must also allow white hair to be covered and, finally, they must be as unselective as possible; in other words, they must allow the smallest possible differences in coloration to be produced over the entire length of a single keratinous fiber, which may in fact be sensitized (i.e., damaged) differently between its tip and its root.

It has already been proposed, particularly in the patents GB 1 026 978 and GB 1 153 196, to use pyridines such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, as oxidation bases for the oxidation dyeing of keratinous fibers.

The applicant has now just discovered, completely unexpectedly and surprisingly, a new class of 3-aminopyrazolo[1,5-a]pyridines, of formula (I) defined hereinbelow, some of which are novel per se, which may be suitable for use as oxidation bases but which, moreover, make it possible to obtain dyeing compositions which lead to colorations which are strong even at neutral pH and which exhibit good stability vis a vis external agents (light, inclement weather, washing, perming, perspiration, and friction).

It is these discoveries which form the basis for the present invention.

Accordingly, the invention first provides a composition for the oxidation dyeing of keratinous fibers, and especially human keratinous fibers such as hair, characterized in that it comprises, in a medium appropriate for dyeing, at least one 3-aminopyrazolo[1,5-a]pyridine of formula (I) below as oxidation base and/or one of its addition salts with an acid or with a base:

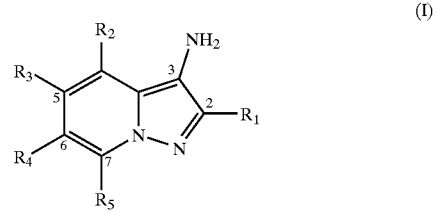

(I)

in which:

$R_1$, $R_2$, $R_3$, $R_4$ and $R_5$, which are identical or different, represent a hydrogen or halogen atom; an —$NHSO_3H$ radical; a hydroxyl radical; a $(C_1$–$C_4)$alkyl radical; a $(C_1$–$C_4)$alkoxy radical; a $(C_1$–$C_4)$alkylthio radical; mono$(C_1$–$C_4)$alkylamino; a di$(C_1$–$C_4)$alkylamino radical in which the two alkyl groups, in conjunction with the nitrogen atom to which they are bonded, may form a ring which may be interrupted by one or more nitrogen, oxygen or sulfur atoms; a heterocycle; a nitro radical; a phenyl radical; a carbonyl radical; a $((C_1$–$C_4)$ alkoxy)carbonyl radical; a carboxamido radical; a cyano radical; an amino radical; a sulfonyl radical; a —$CO_2H$ radical, an —$SO_3H$ radical; a —$PO_3H2$ radical; a —$PO_4H_2$ radical; or a group of formula (II) below:

(II)

in which R represents an oxygen or nitrogen atom, X represents an oxygen atom or an NH or NH$(C_1$–$C_4)$alkyl group, and Y represents a hydroxyl, amino, $C_1$–$C_4$ alkyl, $(C_1$–$C_4)$alkoxy, $(C_1$–$C_4)$alkylamino or di$(C_1$–$C_4)$alkylamino radical.

In the compounds of formula (I) above, the alkyl term used for the alkyl radicals and for the groups containing an alkyl moiety signifies a linear or branched carbon chain containing 1 to 4 carbon atoms which is unsubstituted or substituted by one or more heterocycles or by one or more phenyl groups or by one or more groups selected from halogen atoms such as chlorine, bromine, iodine and fluorine; hydroxyl, alkoxy, amino, carbonyl, carboxamido, sulfonyl, —$CO_2H$, —$SO_3H$, —$PO_3H_2$, —$PO_4H_2$, —$NHSO_3H$, sulfonamide, monoalkyl $(C_1$–$C_4)$amino or trialkyl$(C_1$–$C_4)$ammonium radicals or else by a dialkyl $(C_1$–$C_4)$amino radical in which the two alkyl groups, in conjunction with the nitrogen atom of said dialkyl$(C_1$–$C_4)$ amino group to which they are bonded, may form a ring which may be interrupted by one or more nitrogen, oxygen or sulfur atoms.

Similarly, as claimed in the invention, the alkoxy term used for the alkoxy radicals and for the groups containing an alkoxy moiety signifies a linear or branched O-carbon chain containing 1 to 4 of carbon, which is unsubstituted or substituted by one or more groups selected from heterocycles; halogen atoms such as chlorine, bromine, iodine and fluorine; hydroxyl, amino, carbonyl, carboxamido, sulfonyl, —$CO_2H$, —$SO_3H$, —$PO_3H_2$, —$PO_4H_2$, —$NHSO_3H$, sulfonamide, monoalkyl($C_1$–$C_4$)amino or trialkyl($C_1$–$C_4$) ammonium radicals or else by a dialkyl($C_1$–$C_4$)amino radical in which the two alkyl groups, in conjunction with the nitrogen atom of said dialkyl($C_1$–$C_4$)amino group to which they are bonded, may form a ring which may be interrupted by one or more nitrogen, oxygen or sulfur atoms.

As claimed in the invention, a heterocycle is an aromatic or nonaromatic ring containing 5, 6 or 7 members and from 1 to 3 heteroatoms selected from nitrogen, sulfur and oxygen atoms. These heterocycles can be condensed with other heterocycles or with a phenyl group. They can be substituted by a halogen atom; a ($C_1$–$C_4$)alkyl radical; a ($C_1$–$C_4$)alkoxy radical; a hydroxyl radical; an amino radical; a ($C_1$–$C_4$) alkylamino radical; di($C_1$–$C_4$)alkylamino in which the two alkyl groups, in conjunction with the nitrogen atom to which they are bonded, may form a ring which may be interrupted by one or more nitrogen, oxygen or sulfur atoms. These heterocycles may additionally be quaternized by a ($C_1$–$C_4$) alkyl radical.

Among these heterocycles, mention may be made in particular, by way of example, of the following rings: thiadiazole, triazole, isoxazole, oxazole, azaphosphole, thiazole, isothiazole, imidazole, pyrazole, triazine, thiazine, pyrazine, pyridazine, pyrimidine, pyridine, diazepin, oxazepin, benzotriazole, benzoxazole, benzimidazole, benzothiazole, morpholine, piperidine, piperazine, azetidine, pyrrolidine, aziridine, 3-(2-hydroxyethyl) benzothiazol-3-ium and 1-(2-hydroxyethyl)pyridinium.

As claimed in the invention, phenyl means a phenyl radical which is unsubstituted or substituted by one or more cyano, carbonyl, carboxamido, sulfonyl, —$CO_2H$, —$SO_3H$, —$PO_3H_2$, —$PO_4H_2$, hydroxyl, amino, monoalkyl($C_1$–$C_4$) amino or dialkyl($C_1$–$C_4$)amino radicals in which the two alkyl groups, in conjunction with the nitrogen atom of said dialkyl($C_1$–$C_4$)amino group to which they are bonded, may form a ring which may be interrupted by one or more nitrogen, oxygen or sulfur atoms.

Among the groups of formula (II) above, mention may be made in particular of the groups acetamide, dimethylurea, O-methylcarbamate, methylcarbonate, N-dimethylcarbamate and the esters.

Among the compounds of formula (I) above, preference is given to 3-aminopyrazolo[1,5-a]pyridines of subformula (Ia) below and their addition salts with an acid or with a base:

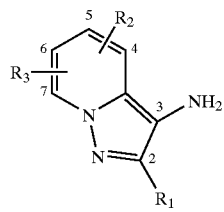

(Ia)

in which:

$R_1$, $R_2$ and $R_3$, which are identical or different, represent a hydrogen or halogen atom; a hydroxyl radical; a ($C_1$–$C_4$)alkyl radical; a ($C_1$–$C_4$)alkylthio radical; a ($C_1$–$C_4$)alkoxy radical; an —$NHSO_3H$ radical; an amino radical; a ($C_1$–$C_4$)alkylamino radical; a di($C_1$–$C_4$)alkylamino radical in which the two alkyl groups, in conjunction with the nitrogen atom to which they are bonded, may form a ring which may be interrupted by one or more nitrogen, oxygen or sulfur atoms; a heterocycle as defined above; a sulfonamide radical; a carbonyl radical; a (($C_1$–$C_4$)alkoxy)carbonyl radical; a carboxamido radical; or a group of formula (II) below:

(II)

in which R represents an oxygen or nitrogen atom, X represents an oxygen atom or an NH or NH($C_1$–$C_4$)alkyl group, and Y represents a hydroxyl, amino, $C_1$–$C_4$ alkyl, ($C_1$–$C_4$)alkoxy, ($C_1$–$C_4$)alkylamino or di($C_1$–$C_4$)alkylamino radical.

Among the 3-aminopyrazolo[1,5-a]pyridines of formula (I) which can be used as oxidation bases in the dyeing compositions of the invention, mention may be made in particular of:

pyrazolo[1,5-a]pyridin-3-ylamine;
2-acetylaminopyrazolo[1,5-a]pyridin-3-ylamine;
2-morpholin-4-ylpyrazolo[1,5-a]pyridin-3-ylamine;
3-aminopyrazolo[1,5-a]pyridine-2-carboxylic acid;
2-methoxypyrazolo[1,5-a]pyridin-3-ylamin;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-morpholin-4-ylpyrazolo[1,5-a]pyridin-3-ylamine;
pyrazolo[1,5-a]pyridine-3,5-diamine;
5-morpholin-4-ylpyrazolo[1,5-a]pyridin-3-ylamine;
2-[(3-aminopyrazolo[1,5-a]pyridin-5-yl)-(2-hydroxyethyl)amino]ethanol;
2-[(3-aminopyrazolo[1,5-a]pyridin-7-yl)-(2-hydroxyethyl)amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;
and their addition [lacuna] with an acid or with a base.

The great majority of the 3-aminopyrazolo[1,5-a] pyridines of formula (I) are compounds which are known in the pharmaceutical field and are described in particular in the patent U.S. Pat. No. 5,457,200. These compounds can be prepared by synthesis methods which are well known in the literature, such as are described, for example, in the patent U.S. Pat. No. 5,457,200.

The 3-aminopyrazolo[1,5-a]pyridine(s) of formula (I) above and/or the or their addition salts with an acid or a base make(s) up preferably from 0.0005 to 12% by weight approximately of the total weight of the dyeing composition and more preferably still from 0.005 to 6% by weight approximately of this weight.

The medium appropriate for dyeing (or vehicle) generally consists of water or of a mixture of water and at least one organic solvent for solubilizing the compounds which would not be sufficiently soluble in water. As organic solvent mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, and diethylene glycol monoethyl ether and monomethyl ether, and aromatic alcohols such as benzyl alcohol or phenoxyethanol, similar products and mixtures thereof.

The solvents may be present in proportions of preferably between 1 and 40% by weight approximately relative to the total weight of the dyeing composition and more preferably still between 5 and 30% by weight approximately.

The pH of the dyeing composition of the invention is generally between approximately 3 and 12 and preferably between approximately 5 and 11. It can be adjusted to the desired value using acidifying or basifying agents which are commonly used in dyeing keratinous fibers or else by means of conventional buffer systems.

Among the acidifying agents mention may be made, by way of example, of mineral or organic acids such as hydrochloric acid, ortho-phosphoric acid, sulfuric acid, carboxylic acids such as acetic acid, tartaric acid, citric acid and lactic acid, and sulfonic acids.

Among the basifying agents mention may be made, by way of example, of aqueous ammonia, alkali metal carbonates, alkanolamines such as mono-, di- and triethanolamines and their derivatives, sodium hydroxide or potassium hydroxide, and the compounds of formula (III) below:

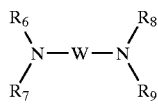

(III)

in which W is a propylene residue optionally substituted by a hydroxyl group or a $C_1$–$C_4$ alkyl radical; and $R_6$, $R_7$, $R_8$ and $R_9$, which are identical or different, represent a hydrogen atom or a $C_1$–$C_4$ alkyl or hydroxyalkyl radical.

In accordance with one preferred embodiment, the oxidation dyeing composition of the invention further comprises one or more couplers in order to modify or enrich with glints the shades obtained employing the compounds of formula (I).

The couplers which can be used in the oxidation dyeing compositions of the invention may be selected from the couplers employed conventionally in oxidation dyeing, among which particular mention maybe made of meta-phenylenediamines, meta-aminophenols, meta-diphenols and heterocyclic couplers.

These couplers are selected more particularly from 2-methyl-5-aminophenol, 5-N-(O-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and their addition salts.

When present, the coupler(s) make(s) up preferably from 0.0001 to 10% by weight approximately of the total weight of the dyeing composition and more preferably still from 0.005 to 5% by weight approximately of this weight.

The dyeing composition of the invention may further comprise, in addition to the dyes defined above, at least one additional oxidation base which may be selected from the oxidation bases used conventionally in oxidation dyeing and among which mention may be made in particular of para-phenylenediamines, bisphenylalkylenediamines, para-aminophenols, ortho-aminophenols and heterocyclic bases other than the 3-aminopyrazolo[1,5-a]pyridines of formula (I) used in accordance with the invention.

Among the para-phenylenediamines, mention may be made more particularly, by way of example, of para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, and their addition salts with an acid.

Among the abovementioned para-phenylenediamines, very particular preference is given to para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(p-hydroxyethyl)-para-phenylenediamine, 2-chloro-para-phenylenediamine, 2-β-acetylaminoethyloxy-para-phenylenediamine, and their addition salts with an acid.

Among the bisphenylalkylenediamines mention may be made more particularly, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl) tetramethylenediamine, N,N'-bis(β-hydroxyethyl)-N,N'-bis (4-aminophenyl)tetramethylenediamine, N,N'-bis(4-methylaminophenyl)tetramethylenediamine, N,N'-bis (ethyl)-N,N'-bis(4'-amino-3'-methylphenyl) ethylenediamine, 1,8-bis(2,5-diaminophenoxy)-3,5-dioxaoctane, and their addition salts with an acid.

Among the para-aminophenols, mention may be made more particularly, by way of example, of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, and their addition salts with an acid.

Among the ortho-aminophenols, mention may be made more particularly, by way of example, of 2-aminophenol, 2-amino-5-methylphenol, 2-amino-6-methylphenol, 5-acetamido-2-aminophenol, and their addition salts with an acid.

Among the heterocyclic bases, mention may be made more particularly, by way of example, of pyridine derivatives other than the compounds of formula (I) of the invention, pyrimidine derivatives and pyrazole derivatives.

Among the pyridine derivatives other than the compounds of formula (I) of the invention, mention may be made more particularly of the compounds described for example in the patents GB 1 026 978 and GB 1 153 196, such as 2,5-diaminopyridine, 2-(4-methoxyphenyl)amino-3-aminopyridine, 2,3-diamino-6-methoxypyridine, 2-(methoxyethyl)amino-3-amino-6-methoxypyridine, 3,4-diaminopyridine, and their addition salts with an acid.

Among the pyrimidine derivatives mention may be made more particularly of the compounds described for example in the patents DE 2 359 399; JP 88-169 571; JP 05 163 124; EP 0 770 375, or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and the pyrazolopyrimidine derivatives such as those mentioned in the patent application FR-A-2 750 048, among which mention may be made of pyrazolo[1,5-a]pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)-(2-hydroxyethyl)amino]ethanol, 2-[(7-aminopyrazolo[1,5-a]pyrimidin-3-yl)-(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine, 3-amino-5-methyl-7-imidazolylpropyl-aminopyrazolo[1,5-a]pyrimidine and their addition salts with an acid and, where a tautomeric equilibrium exists, their tautomeric forms.

Among the pyrazole derivatives mention may be made more particularly of the compounds described in the patents DE 3 843 892, DE 4 133 957 and patent applications WO 94/08969, WO 94/08970, FR-A-2 733 749 and DE 195 43 988 such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and their addition salts with an acid.

Where used, the additional oxidation base(s) make(s) up preferably from 0.0005 to 12% by weight approximately of the total weight of the dyeing composition and more preferably still from 0.005 to 6% by weight approximately of this weight.

Generally speaking, the addition salts with an acid that can be used in the context of the dyeing compositions of the invention (compounds of formula (I), (Ia), additional oxidation bases, and couplers) are selected in particular from hydrochlorides, hydrobromides, sulfates, citrates, succinates, tartrates, lactates, phosphates and acetates. The addition salts with a base that can be used in the context of the dyeing compositions of the invention are in particular those obtained with sodium hydroxide, potassium hydroxide, aqueous ammonia or amines.

The dyeing composition of the invention may further comprise one or more direct dyes which can be selected in particular from the nitro dyes of the benzene series.

The dyeing composition of the invention may further comprise various adjuvants conventionally used in compositions for dyeing hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, penetrants, sequestrants, perfumes, buffers, dispersants, conditioners such as, for example, volatile or nonvolatile, modified or unmodified silicones, film formers, ceramides, preservatives and opacifiers.

The person skilled in the art will of course take care to select the abovementioned optional complementary compound(s) in such a way that the advantageous properties intrinsic to the oxidation dyeing composition of the invention are not, or not substantially, impaired by the intended addition or additions.

The dyeing composition of the invention may be in any of a variety of forms, such as in liquid, cream, gel or any other form appropriate for dyeing keratinous fibers and especially human hair.

The invention likewise provides a method of dyeing keratinous fibers and especially human keratinous fibers such as hair, employing the dyeing composition as defined above.

As claimed in this method, at least one dyeing composition as defined above is applied to the fibers, the color being developed at acid, neutral or alkaline pH by means of an oxidizing agent which is added to the dyeing composition at the time of use or which is present in an oxidizing composition applied simultaneously or sequentially.

As claimed in one preferred embodiment of the dyeing method of the invention, the dyeing composition described above is mixed preferably at the time of use with an oxidizing composition comprising, in a medium appropriate for dyeing, at least one oxidizing agent in an amount sufficient to develop a coloration. The mixture obtained is then applied to the keratinous fibers and left to act for approximately 3 to 50 minutes, preferably approximately 5 to 30 minutes, after which said fibers are rinsed, washed with shampoo, rinsed again and dried.

The oxidizing agent may be selected from oxidizing agents conventionally used for the oxidation dyeing of keratinous fibers, among which mention may be made of hydrogen peroxide, urea peroxide, alkali metal bromates, persalts such as perborates and persulfates, and enzymes, among which mention may be made of peroxidases, 2-electron oxidoreductases such as uricases, and 4-electron oxygenases such as laccases. Hydrogen peroxide is particularly preferred.

The pH of the oxidizing composition comprising the oxidizing agent as defined above is such that, following its mixture with the dyeing composition, the pH of the resulting composition applied to the keratinous fibers varies preferably between approximately 3 and 12 and more preferably still between 5 and 11. It is adjusted to the desired value by means of acidifying or basifying agents which are commonly used in dyeing keratinous fibers and which are such as defined above.

The oxidizing composition as defined above may further comprise various adjuvants which are conventionally used in compositions for dyeing hair and which are such as defined above.

The composition which is finally applied to the keratinous fibers may be present in various forms, such as in liquid, cream, gel or any other form appropriate for dyeing keratinous fibers and especially human hair.

The invention further provides a multicompartment dyeing device or kit or any other multicompartment packaging system of which a first compartment contains the dyeing composition as defined above and a second compartment contains the oxidizing composition as defined above. These devices may be equipped with a means enabling the desired mixture to be delivered onto the hair, such as the devices described in the applicant's patent FR-2 586 913.

Certain compounds of formula (I) used as oxidation bases in the context of the present invention are novel and are therefore also provided by the invention.

These novel 3-aminopyrazolo[1,5-a]pyridines and their addition salts with an acid or with a base are of the following formula (I'):

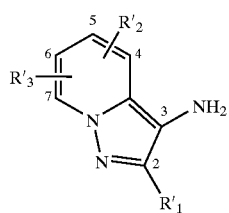

in which:
R'$_1$ represents a hydrogen or halogen atom; a hydroxyl radical; (C$_1$–C$_4$)alkyl; a (C$_1$–C$_4$)alkylthio radical; a (C$_1$–C$_4$)alkoxy radical; an amino radical; a (C$_1$–C$_4$) alkylamino radical; a di(C$_1$–C$_4$)alkylamino radical in which the two alkyl groups, in conjunction with the nitrogen atom to which they are bonded, may form a ring which may be interrupted by one or more nitrogen, oxygen or sulfur atoms; a heterocycle; or a group of formula (II') below:

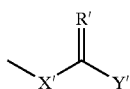

in which R' represents an oxygen or nitrogen atom, X' represents an oxygen atom or an NH or NH(C$_1$–C$_4$)alkyl group, and Y' represents a hydroxyl, amino, C$_1$–C$_4$ alkyl, (C$_1$–C$_4$)alkoxy, (C$_1$–C$_4$)alkylamino or di(C$_2$–C$_4$)alkylamino radical;

R'$_2$ and R'$_3$, which are identical or different, represent a hydrogen atom; a halogen atom; a nitro radical; a heterocycle; an NHSO$_3$H radical; a sulfonamide radical; a (C$_1$–C$_4$)alkyl radical substituted by one or more identical or different radicals selected from heterocycles, —CO$_2$H, —SO$_3$H, —PO$_3$H$_2$, —PO$_4$H$_2$, hydroxyl, tri(C$_1$–C$_4$)alkylammonium, —NHSO$_3$H, sulfonamide, amino, (C$_1$–C$_4$)alkylamino and di(C$_1$–C$_4$)alkylamino radicals in which the two alkyl radicals, in conjunction with the nitrogen atom to which they are bonded, may form a ring which may be interrupted by one or more nitrogen, sulfur or oxygen atoms; a (C$_1$–C$_4$)alkylthio radical substituted by one or more hydroxyl or substituted or unsubstituted amino radicals or by one or more —CO$_2$H, —SO$_3$H, —PO$_3$H$_2$ or —PO$_4$H$_2$ groups or by one or more heterocycles; a (C$_1$–C$_4$)alkoxy radical substituted by one or more hydroxyl or substituted or unsubstituted amino radicals or by one or more —CO$_2$H, —SO$_3$H, —PO$_3$H$_2$ or —PO$_4$H$_2$ groups or by one or more heterocycles; an amino radical substituted by one or two (C$_1$–C$_4$)alkyl radicals, said alkyl radical or radicals being itself or themselves substituted by a substituted or unsubstituted amino, tri(C$_1$–C$_4$)alkylammonium, —CO$_2$H, —SO$_3$H, —PO$_3$H$_2$, —PO$_4$H$_2$ or —NHSO$_3$H radical or by a heterocycle; with the proviso that:

at least one of the radicals R'$_1$ to R'$_3$ is other than a hydrogen atom;

the radicals R'$_2$ and R'$_3$ cannot simultaneously represent a hydrogen atom;

when R'$_1$ represents a heterocycle, R'$_2$ and R'$_3$ are other than a halogen atom and a hydrogen atom;

when R'$_1$ represents a hydrogen atom and when one of the radicals R'$_2$ or R'$_3$ also represents a hydrogen atom, the other radical R'$_2$ or R'$_3$ is other than a hydroxymethyl radical in position 7 or than a β-hydroxyethyl radical in position 7 or 5;

when R'$_1$ represents a methoxy radical and when one of the radicals R'$_2$ or R'$_3$ represents a hydrogen atom, the other radical R'$_2$ or R'$_3$ is other than a chlorine atom.

In the compounds of formula (I') above, the heterocycle term signifies an aromatic or nonaromatic ring containing 5, 6 or 7 members and from 1 to 3 heteroatoms selected from nitrogen, sulfur and oxygen atoms. These heterocycles can be condensed with other heterocycles or with a phenyl group. They can be substituted by a halogen atom; a (C$_1$–C$_4$)alkyl radical; a (C$_1$–C$_4$)alkoxy radical; a hydroxyl radical; an amino radical; a (C$_1$–C$_4$)alkylamino radical; di(C$_1$–C$_4$)alkylamino in which the two alkyl groups, in conjunction with the nitrogen atom to which they are bonded, may form a ring which may be interrupted by one or more nitrogen, oxygen or sulfur atoms. These heterocycles may additionally be quaternized by a (C$_1$–C$_4$)alkyl radical.

Among these heterocycles, mention may be made in particular, by way of example, of the following rings: thiadiazole, triazole, isoxazole, oxazole, azaphosphole, thiazole, isothiazole, imidazole, pyrazole, triazine, thiazine, pyrazine, pyridazine, pyrimidine, pyridine, diazepin, oxazepin, benzotriazole, benzoxazole, benzimidazole, benzothiazole, morpholine, piperidine, piperazine, azetidine, pyrrolidine, aziridine, 3-(2-hydroxyethyl) benzothiazol-3-ium and 1-(2-hydroxyethyl)pyridinium.

Among the groups of formula (II') above, mention may be made in particular of the groups acetamide, dimethylurea, O-methylcarbamate, methylcarbonate, N-dimethylcarbamate and the esters.

Among the 3-aminopyrazolo[1,5-a]pyridines of formula (I') above, mention may be made in particular of:

5-pyridin-4-ylpyrazolo[1,5-a]pyridin-3-ylamine;

4-(3-aminopyrazolo[1,5-a]pyridin-5-yl)-1-methylpyridinium;

4-(3-aminopyrazolo[1,5-a]pyridin-5-yl)-1-(2-hydroxyethyl)pyridinium;

(3-aminopyrazolo[1,5-a]pyridin-2-yl)pyridin-2-ylmethanol;

2-[(3-aminopyrazolo[1,5-a]pyridin-2-yl)hydroxymethyl]-1-methylpyridinium;

2-[(3-aminopyrazolo[1,5-a]pyridin-2-yl)hydroxymethyl]-1-(2-hydroxyethyl)pyridinium;

N-7-(2-imidazo-1-ylpropyl)pyrazolo[1,5-a]pyridine-3,7-diamine;

3-[2-(3-aminopyrazolo[1,5-a]pyridin-7-ylamino)propyl]-1-methyl-3H-imidazol-1-ium;

3-[2-(3-aminopyrazolo[1,5-a]pyridin-7-ylamino)propyl]-1-(2-hydroxyethyl)-3H-imidazol-1-ium;

N-5-(3-imidazo-1-ylpropyl)pyrazolo[1,5-a]pyridine-3,5-diamine;

3-[3-(3-aminopyrazolo[1,5-a]pyridin-5-ylamino)propyl]-1-methyl-3H-imidazol-1-ium;

3-[3-(3-aminopyrazolo[1,5-a]pyridin-5-ylamino)propyl]-1-(2-hydroxyethyl)-3H-imidazol-1-ium;

and their addition salts with an acid or with a base.

The addition salts with an acid of the compounds of formula (I') above are selected preferably from hydrochlorides, hydrobromides, sulfates, citrates, succinates, tartrates, lactates, phosphates and acetates. The addition salts with a base of the compounds of formula (II) above are selected preferably from those obtained with sodium hydroxide, potassium hydroxide, aqueous ammonia or amines.

These novel 3-aminopyrazolo[1,5-a]pyrimidines of formula (I') above, and, more generally, the 3-aminopyrazolo[1,5-a]pyridines of formula (I) described above, may be prepared by methods which are known and are described in the literature, and, for example, in accordance with the following synthesis scheme:

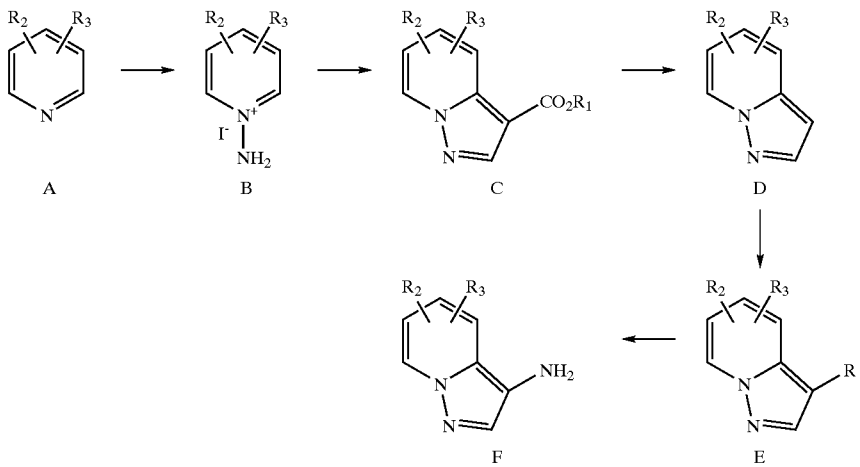

in accordance with which a compound A is aminated for example with —NH$_2$SO$_3$H or NH$_2$SO$_3$MS (o-mesitylenesulfonylhydroxylamine) to give a compound B, with conversion of the sulfate salt to the iodide salt. These amination reactions are described in particular in J. Org. Chem. 33 (1968) 3766; Chem. Pharm. Bull. 22 (1974) 482; Tet. Lett. (1972) 4133; Synthesis (1977) 1; or else in Bull. Chem. Soc. Jpn. 49 (1976) 1980.

The compound C can then be obtained by 1,3-dipolar cyclization of the compound B with methyl or ethyl propiolate. This cyclization reaction is described in Liebigs Ann. Chem. (1977) 498; Tet. Lett. (1962) 387; Arch. Pharm. 321 (1988) 505; J. Het. Chem. 18 (1981) 1149; Het. 24 (1986) 3411; Biorg. Med. Chem. Lett. 3 (1993) 1477.

The compound C is converted into compound D following hydrolysis of the ester to give the corresponding acid, followed by a decarboxylation; see Liebigs Ann. Chem. (1977) 498; J. Het. Chem. 18 (1981) 1149.

The introduction of a radical R denoting a nitro, nitroso or arylazo group starting from the compound D to give the compound E is carried out in accordance with methods described in the literature. The nitration can, for example, be carried out with nitric acid, nitric acid mixed with sulfuric acid, or nitric acid mixed with acetic acid. The nitrosation can, for example, be carried out with nitrous acid. An arylazo radical can be introduced by reacting the aryldiazonium salt with the compound D.

These methods are described in "Nitration Method and Mechanism", G. Olah, R. Malhotra, S. Narang, VCH Publishers; Houben-Weyl, Methoden der Organischen Chemie, Vol. 10/1 and 10/3; U.S. Pat. No. 5,457,200; J. Heterocycl. Chem. 11 (1974) 223–225.

The nitro, nitroso and arylazo groups are subsequently reduced to give a compound F in accordance with methods described in the literature. The reduction can be carried out, for example, with zinc in acetic acid, glacial acetic acid and sodium dithionite, tin chloride in an acid, or else by catalytic hydrogenation. See in particular Houben-Weyl, Methoden der Organischen Chemie, Vol. 10/1 and 10/3; U.S. Pat. No. 5,457,200.

The starting pyridines (compounds A) have been described or can be prepared by analogy with known compounds. Regarding the preparation of pyridines, see Comprehensive Heterocyclic Chemistry II Vol. 5, A. Katritzky, C. Rees, E. Scriven.

The compounds of general formula (I) or (I') substituted in position 2 can be prepared by analogy with J. Het. Chem. (1975) 481; Chem. Pharm. Bull. 21 (1973) 2146.

The invention lastly provides for the use of 3-aminopyrazolo[1,5]pyridines of formulae (I), (Ia) or (I') and their addition salts with an acid or with a base as oxidation bases for the oxidation dyeing of keratinous fibers and especially human keratinous fibers such as hair.

The examples which follow are intended to illustrate the invention.

SYNTHESIS EXAMPLES

Example 1

Synthesis of 3,4-Diaminopyrazolo[1,5-a]pyridine Dihydrochloride

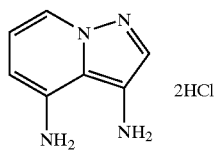

0.7 g of 3,4-dinitropyrazolo[1,5-a]pyridine was added to a suspension of 11.1 g of tin chloride in 80 ml of concentrated hydrochloric acid. The reaction was monitored by thin layer chromatography (TLC). The pH of the reaction mixture was adjusted to 12 using sodium hydroxide. The aqueous phase was extracted with ethyl acetate and the organic phase was dried over sodium sulfate. The organic phase was acidified with 3 ml of hydrochloric ethanol (2.5 N HCl). The precipitate was filtered off. This gave 0.55 g of pyrazolo[1,5-a]pyridine-3,4-diamine hydrochloride, whose $^1$H NMR analysis (DMSO-$d_6$, 400 MHz) (δ ppm) was as follows:

1H NMR (DMSO $d_6$): 6.82 (d, 1H); 6.97 (d, 1H); 8.18 (s, 1H); 8.36 (d, 1H).

Example 2

Synthesis of 3,6-Diaminopyrazolo[1,5-a]pyridine

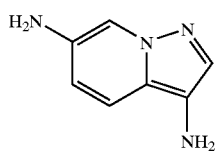

a) First Step: Preparation of 3,6-Dinitropyrazolo[1,5-a]pyridine by Nitration of Pyrazolo[1,5-a]pyridine in Accordance With J. Heterocycl. Chem. 11 (1974) 223–225

3.75 ml of concentrated nitric acid were added to a solution of 4.5 g of pyrazolo[1,5-a]pyridine in 20 ml of concentrated sulfuric acid. The reaction was monitored by gas chromatography. After 4 hours of reaction, 1 ml of nitric acid was added. The reaction mixture was poured onto 200 ml of ice and the precipitate was filtered off.

The product was obtained as a mixture with 3,4-dinitropyrazolo[1,5-a]pyridine and isolated by flash chromatography on silica. $^1$H NMR analysis (DMSO $d_6$, 400 MHz) (δ ppm) was as follows:

1H NMR (DMSO d6): 10.15 (d, 1H); 9.16 (s, 1H); 8.50 (dd, 1H); 8.36 (d, 1H).

b) Second Step: Preparation of Pyrazolo[1,5-a]pyridine-3,6-diamine

The reduction of 3,6-dinitropyrazolo[1,5-a]pyridine was carried out using zinc in an ethanol/water mixture.

MS (chemical ionization at atmospheric pressure): MH$^+$ 149.1.

DYEING EXAMPLES

Examples 1 to 5

Dyeing in an Alkaline Medium

The following dyeing compositions of the invention were prepared:

| COMPOSITION | 1 | 2 | 3 | 4 | 5 |
|---|---|---|---|---|---|
| 3,4-Diaminopyrazolo[1,5-a]pyridine dihydrochloride (oxidation base of formula (I)) | $3 \times 10^{-3}$ mol | — | — | — | — |
| Pyrazolo[1,5-a]pyridin-3-ylamine hydrochloride (oxidation base of formula (I)) | — | $3 \times 10^{-3}$ mol | $3 \times 10^{-3}$ mol | $3 \times 10^{-3}$ mol | — |
| 2-Acetylaminopyrazolo [1,5-a] pyridin-3-ylamine hydrochloride (oxidation base of formula (I)) | — | — | — | — | $3 \times 10^{-3}$ mol |
| 2,4-Diamino-1-(β-hydroxyethyloxy)benzene (coupler) | $3 \times 10^{-3}$ mol | — | $3 \times 10^{-3}$ mol | — | $3 \times 10^{-3}$ mol |
| 3-Aminophenol (coupler) | — | $3 \times 10^{-3}$ mol | — | — | — |
| 6-Hydroxyindole (coupler) | — | — | — | $3 \times 10^{-3}$ mol | — |
| Common dyeing vehicle 1 | (*) | (*) | (*) | (*) | (*) |
| Demineralized water q.s. | 100 g | 100 g | 100 g | 100 g | 100 g |

(*) Common dyeing vehicle 1:

96° ethyl alcohol 18 g

35% aqueous sodium metabisulfite solution 0.68 g

Pentasodium salt of diethylenetriamine-pentaacetic acid 1.1 g

20% aqueous ammonia 10.0 g

Demineralized water q.s. 100 g

Each of the above dyeing compositions was mixed weight for weight at the time of use with a 20 volume hydrogen peroxide solution (6% by weight) with a pH of 3.

Each of the mixtures obtained was applied to locks of natural gray hair containing 90% white hairs for 30 minutes. The locks were subsequently rinsed, washed with a standard shampoo, rinsed again and then dried.

The shades obtained are given in the table below:

| EXAMPLE | Dyeing pH | Shade obtained |
|---|---|---|
| 1 | 10 ± 0.2 | Ash blond |
| 2 | 10 ± 0.2 | Iridescent mahogany |

| EXAMPLE | Dyeing pH | Shade obtained |
|---|---|---|
| 3 | 10 ± 0.2 | Dark purple |
| 4 | 10 ± 0.2 | Coppery gold |
| 5 | 10 ± 0.2 | Slightly mauvish ashen |

Examples 6 to 10

Dyeing in a Neutral Medium

The following dyeing compositions of the invention were prepared:

| COMPOSITION | 6 | 7 | 8 | 9 | 10 |
|---|---|---|---|---|---|
| 3,4-Diaminopyrazolo[1,5-a]pyridine dihydrochloride (oxidation base of formula (I)) | $3 \times 10^{-3}$ mol | — | — | — | — |
| Pyrazolo[1,5-a]pyridin-3-ylamine hydrochloride (oxidation base of formula (I)) | — | $3 \times 10^{-3}$ mol | $3 \times 10^{-3}$ mol | $3 \times 10^{-3}$ mol | — |
| 2-Acetylaminopyrazolo [1,5-a] pyridin-3-ylamine hydrochloride (oxidation base of formula (I)) | — | — | — | — | $3 \times 10^{-3}$ mol |
| 2,4-Diamino-1-(β-hydroxyethyloxy)benzene (coupler) | $3 \times 10^{-3}$ mol | — | $3 \times 10^{-3}$ mol | — | $3 \times 10^{-3}$ mol |
| 5-N-(β-Hydroxyethyl)amino-2-methylphenol (coupler) | — | $3 \times 10^{-3}$ mol | — | — | — |
| 6-Hydroxyindole (coupler) | — | — | — | $3 \times 10^{-3}$ mol | — |
| Common dyeing vehicle 2 | () | () | () | () | (**) |
| Demineralized water q.s. | 100 g | 100 g | 100 g | 100 g | 100 g |

(**) Common dyeing vehicle 2:

96° ethanol 18 g $K_2HPO_4/KH_2PO_4$ buffer (1.5M/1M) 10 g

Sodium metabisulfite 0.68 g

Pentasodium salt of diethylenetriamine-pentaacetic acid 1.1 g

Each of the above dyeing compositions was mixed weight for weight at the time of use with a 20 volume hydrogen peroxide solution (6% by weight) with a pH of 3.

The mixture obtained was applied to locks of natural gray hair containing 90% white hairs for 30 minutes. The locks were subsequently rinsed, washed with a standard shampoo, rinsed again and then dried.

The shades obtained are given in the table below:

| EXAMPLE | Dyeing pH | Shade obtained |
|---|---|---|
| 6 | 5.7 ± 0.2 | Slightly matte ashen |
| 7 | 5.7 ± 0.2 | Coppery gold |
| 8 | 5.7 ± 0.2 | Iridescent dark purple |
| 9 | 5.7 ± 0.2 | Mahogany gold |
| 10 | 5.7 ± 0.2 | Very slightly iridescent ashen |

What is claimed is:

1. A composition for oxidation dyeing of keratinous fibers, comprising, in a medium appropriate for dyeing, at least one oxidation base chosen from 3-aminopyrazolo[1,5-a]pyridines of formula (I), acid addition salts thereof, and base addition salts thereof:

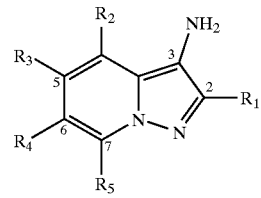

in which:

$R_1$, $R_2$, $R_3$, $R_4$ and $R_5$ are each independently chosen from: hydrogen; a halogen; an —$NHSO_3H$ radical; a hydroxyl radical; a ($C_1$–$C_4$)alkyl radical; a ($C_1$–$C_4$) alkoxy radical; a ($C_1$–$C_4$)alkylthio radical; a ($C_1$–$C_4$) alkylamino radical; a di($C_1$–$C_4$)alkylamino radical wherein optionally the two alkyl groups, in conjunction with the nitrogen atom to which they are bonded, form a ring optionally interrupted by at least one heteroatom chosen from nitrogen, oxygen and sulfur; a heterocycle; a nitro radical; a phenyl radical; a carbonyl radical; a (($C_1$–$C_4$)alkoxy)carbonyl radical; a carboxamido radical; a cyano radical; an amino radical; a sulfonyl radical; a —$CO_2H$ radical, an —$SO_3H$ radical; a —$PO_3H_2$ radical; a —$PO_4H_2$ radical; and a group of formula (II):

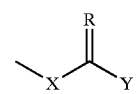

in which:

R is chosen from oxygen and nitrogen; X is chosen from oxygen, an NH radical, and an NH($C_1$–$C_4$)alkyl radical; and Y is chosen from a hydroxyl radical, an amino radical, a $C_1$–$C_4$ alkyl radical, a ($C_1$–$C_4$)alkoxy radical, a ($C_1$–$C_4$)alkylamino radical, and a di($C_1$–$C_4$) alkylamino radical.

2. The composition according to claim 1, wherein the at least one oxidation base is chosen from 3-aminopyrazolo[1,5-a]pyridines of formula (Ia), acid addition salts thereof, and base addition salts thereof:

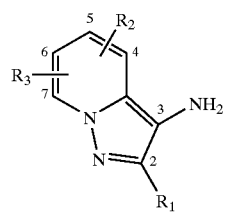

(Ia)

in which:
R₁, R₂ and R₃ are each independently chosen from: hydrogen; a halogen; a hydroxyl radical; a $(C_1-C_4)$ alkyl radical; a $(C_1-C_4)$alkylthio radical; a $(C_1-C_4)$ alkoxy radical; an —NHSO₃H radical; an amino radical; a $(C_1-C_4)$alkylamino radical; a di$(C_1-C_4)$ alkylamino radical wherein optionally the two alkyl groups, in conjunction with the nitrogen atom to which they are bonded, form a ring optionally interrupted by at least one heteroatom chosen from nitrogen, oxygen and sulfur; a heterocycle; a sulfonamide radical; a carbonyl radical; a $((C_1-C_4)$alkoxy)carbonyl radical; a carboxamido radical; and a group of formula (II):

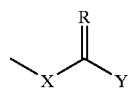

(II)

in which R is chosen from oxygen and nitrogen; X is chosen from oxygen, an NH radical, and an NH$(C_1-C_4)$alkyl radical; and Y is chosen from a hydroxyl radical, an amino radical, a $C_1-C_4$ alkyl radical, a $(C_1-C_4)$alkoxy radical, a $(C_1-C_4)$ alkylamino radical, and a di$(C_1-C_4)$alkylamino radical.

3. The composition according to claim 1, wherein the at least one oxidation base is chosen from:
pyrazolo[1,5-a]pyridin-3-ylamine;
2-acetylaminopyrazolo[1,5-a]pyridin-3-ylamine;
2-morpholin-4-ylpyrazolo[1,5-a]pyridin-3-ylamine;
3-aminopyrazolo[1,5-a]pyridine-2arboxylic acid;
2-methoxypyrazolo[1,5-a]pyridin-3-ylamino;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-morpholin-4-ylpyrazolo[1,5-a]pyridin-3-ylamine;
pyrazolo[1,5-a]pyridine-3,5-diamine;
5-morpholin-4-ylpyrazolo[1,5-a]pyridin-3-ylamine;
2-[(3-aminopyrazolo[1,5-a]pyridin-5-yl(2-hydroxyethyl)amino]ethanol;
2-[(3-aminopyrazolo[1,5-a]pyridin-7-yl)-(2-hydroxyethyl)amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;

their acid addition salts; and
their base addition salts.

4. The composition according to claim 1, wherein the at least one oxidation base is present in an amount ranging from 0.0005 to 12% by weight of the total weight of the dyeing composition.

5. The composition according to claim 4, wherein the at least one oxidation base is present in an amount ranging from 0.005 to 6% by weight of the total weight of the dyeing composition.

6. The composition according to claim 1, further comprising at least one coupler chosen from meta-phenylenediamines, meta-aminophenols, meta-diphenols, and heterocyclic couplers.

7. The composition according to claim 6, wherein the at least one coupler is chosen from 2-methyl-5aminophenol, 5-N-(β-hydroxyethyl)amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, sesamol, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, and their addition salts.

8. The composition according to claim 6, wherein the at least one coupler is present in an amount ranging from 0.0001 to 10% by weight of the total weight of the dyeing composition.

9. The composition according to claim 8, wherein the at least one coupler is present in an amount ranging from 0.005 to 5% by weight of the total weight of the dyeing composition.

10. The composition according to claim 1, further comprising at least one additional oxidation base chosen from para-phenylenediamines, bisphenylalkylenediamines, para-aminophenols, oitho-aminophenols, and heterocyclic bases other than the at least one oxidation base.

11. The composition according to claim 10, wherein the at least one additional oxidation base is present in an amount ranging from 0.0005 to 12% by weight of the total weight of the dyeing composition.

12. The composition according to claim 11, wherein the at least one additional oxidation base is present in an amount ranging from 0.005 to 6% by weight of the total weight of the dyeing composition.

13. The composition according to claim 1, wherein the acid addition salts are chosen from hydrochlorides, hydrobromides, sulfates, citrates, succinates, tartrates, lactates, phosphates, and acetates.

14. The composition according to claim 1, wherein the base addition salts are chosen from sodium hydroxide, potassium hydroxide, aqueous ammonia, and amines.

15. A method of oxidation dyeing keratinous fibers, comprising:
applying to the keratinous fibers, in an amount effective to dye the fibers, a dyeing composition comprising, in a medium appropriate for dyeing, at least one oxidation base chosen from 3-aminopyrazolo[1,5a]pyridines of formula (I), acid addition salts thereof, and base addition salts thereof:

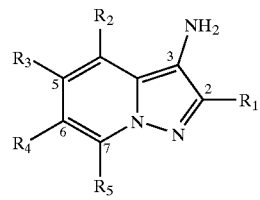

in which:

R₁, R₂, R₃, R₄ and R₅ are each independently chosen from: hydrogen; a halogen; an —NHSO₃H radical; a hydroxyl radical; a (C₁–C₄)alkyl radical; a (C₁–C₄)alkoxy radical; a (C₁–C₄)alkylthio radical; a (C₁–C₄)alkylamino radical; a di(C₁–C₄)alkylamino radical wherein optionally the two alkyl groups, in conjunction with the nitrogen atom to which they are bonded, form a ring optionally interrupted by at least one heteroatom chosen from nitrogen, oxygen and sulfur; a heterocycle; a nitro radical; a phenyl radical; a carbonyl radical; a ((C₁–C₄)alkoxy)carbonyl radical; a carboxamido radical; a cyano radical; an amino radical; a sulfonyl radical; a —CO₂H radical, an —SO₃H radical; a —PO₃H₂ radical; a —PO₄H₂ radical; and a group of formula (II):

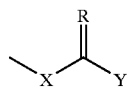

in which:

R is chosen from oxygen and nitrogen; X is chosen from oxygen, an NH radical, and an NH(C₁–C₄)alkyl radical; and Y is chosen from a hydroxyl radical, an amino radical, a C₁–C₄ alkyl radical, a (C₁–C₄)alkoxy radical, a (C₁–C₄)alkylamino radical, and a di(C₁–C₄)alkylamino radical; and adding an oxidizing agent to the dyeing composition to develop a resulting color at acid, neutral or alkaline pH.

16. The method according to claim 15, wherein the oxidizing agent is added at the time of use.

17. The method according to claim 15, wherein the oxidizing agent is present in an oxidizing composition applied simultaneously or sequentially.

18. The method according to claim 15, wherein the oxidizing agent is chosen from hydrogen peroxide, urea peroxide, alkali metal bromates, persalts, peracids, and enzymes.

19. A kit comprising:

a first compartment containing a dyeing composition comprising, in a medium appropriate for dyeing, at least one oxidation base chosen from 3-aminopyrazolo[1,5a]pyridines of formula (I), acid addition salts thereof, and base addition salts thereof:

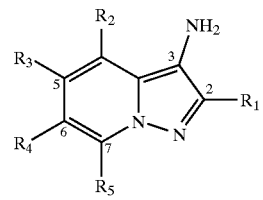

in which:

R₁, R₂, R₃, R₄ and R₅ are each independently chosen from: hydrogen; a halogen; an —NHSO₃H radical; a hydroxyl radical; a (C₁–C₄)alkyl radical; a (C₁–C₄)alkoxy radical; a (C₁–C₄)alkylthio radical; a (C₁–C₄)alkylamino radical; a di(C₁–C₄)alkylamino radical wherein optionally the two alkyl groups, in conjunction with the nitrogen atom to which they are bonded, form a ring optionally interrupted by at least one heteroatom chosen from nitrogen, oxygen and sulfur; a heterocycle; a nitro radical; a phenyl radical; a carbonyl radical; a ((C₁–C₄)alkoxy)carbonyl radical; a carboxamido radical; a cyano radical; an amino radical; a sulfonyl radical; a —CO₂H radical, an —SO₃H radical; a —PO₃H₂ radical; a —PO₄H₂ radical; and a group of formula (II):

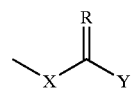

in which:

R is chosen from oxygen and nitrogen; X is chosen from oxygen, an NH radical, and an NH(C₁–C₄)alkyl radical; and Y is chosen from a hydroxyl radical, an amino radical, a C₁–C₄ alkyl radical, a (C₁–C₄)alkoxy radical, a (C₁–C₄)alkylamino radical, and a di(C₁–C₄)alkylamino radical; and a second compartment containing an oxidizing composition.

20. 3-Aminopyrazolo[1,5-a]pyridines of formula (I'); acid addition salts thereof, and base addition salts thereof:

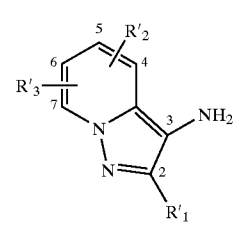

in which:

R'₁ is chosen from: hydrogen; a halogen; a hydroxyl radical; a (C₁–C₄)alkyl radical; a (C₁–C₄)alkylthio radical; a (C₁–C₄)alkoxy radical; an amino radical; a (C₁–C₄)alkylamino radical; a di(C₁–C₄)alkylamino radical wherein optionally the two alkyl radicals, in conjunction with the nitrogen atom to which they are bonded, form a ring optionally interrupted by at least one heteroatom chosen from nitrogen, oxygen, and sulfur; a heterocycle; and a group of formula (II') below:

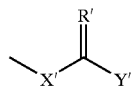

(II')

in which:
R' is chosen from oxygen and nitrogen; X' is chosen from oxygen, an NH radical, and an NH($C_1$–$C_4$)alkyl radical; and Y' is chosen from a hydroxyl radical, an amino radical, a $C_1$–$C_4$ alkyl radical, a ($C_1$–$C_4$)alkoxy radical, a ($C_1$–$C_4$)alkylamino radical, and a di($C_1$–$C_4$)alkylamino radical;

$R'_2$ and $R'_3$ are each independently chosen from hydrogen; a halogen; a nitro radical; a heterocycle; an $NHSO_3H$ radical; a sulfonamide radical; a ($C_1$–$C_4$) alkyl radical substituted by at least one radical chosen from heterocycles, —$CO_2H$, —$SO_3H$, —$PO_3H_2$, —$PO_4H_2$, hydroxyl, tri($C_1$–$C_4$)alkylammonium, —$NHSO_3H$, sulfonamide, amino, ($C_1$–$C_4$)alkylamino, a di($C_1$–$C_4$)alkylamino wherein optionally the two alkyl radicals, in conjunction with the nitrogen atom to which they are bonded, form a ring optionally interrupted by at least one heteroatom chosen from nitrogen, sulfur, and oxygen; a ($C_1$–$C_4$)alkylthio radical substituted by at least one radical chosen from hydroxyl, substituted and unsubstituted amino radicals, —$CO_2H$, —$SO_3H$, —$PO_3H_2$, and —$PO_4H_2$, and a heterocycle; a ($C_1$–$C_4$)alkoxy radical substituted by at least one radical chosen from hydroxyl, substituted and unsubstituted amino radicals, —$CO_2H$, —$SO_3H$, —$PO_3H_2$, and —$PO_4H_2$, and a heterocycle; an amino radical substituted by at least one ($C_1$–$C_4$)alkyl radical, said at least one alkyl radical optionally substituted by at least one radical chosen from substituted and unsubstituted amino groups, tri($C_1$–$C_4$)alkylammonium, —$CO_2H$, —$SO_3H$, —$PO_3H_2$, —$PO_4H_2$, —$NHSO_3H$, and a heterocycle;

with the proviso that:
at least one of the radicals $R'_1$ to $R'_3$ is a group other than hydrogen;
the radicals $R'_2$ and $R'_3$ cannot simultaneously be hydrogen;
when $R'_1$ is a heterocycle, $R'_2$ and $R'_3$ are groups other than a halogen and hydrogen;
when $R'_1$ is hydrogen and when one of the radicals $R'_2$ or $R'_3$ are hydrogen, the other radical $R'_2$ or $R'_3$ is a group other than a hydroxymethyl radical in position 7 or other than a β-hydroxyethyl radical in position 7 or 5;
when $R'_1$ is a methoxy radical and when one of the radicals $R'_2$ or $R'_3$ is hydrogen, the other radical $R'_2$ or $R'_3$ is a group other than chlorine.

21. 3-Aminopyrazolo[1,5-a]pyridines of formula (I') according to claim 20, chosen from:
5-pyridin-4-ylpyrazolo[1,5-a]pyridin-3-ylamine;
4-(3-aminopyrazolo[1,5-a]pyridin-5-yl)-1-methylpyridinium;
4-(3-aminopyrazolo[1,5-a]pyridin-5-yl)-1-(2-hydroxyethyl)pyridinium;
(3-aminopyrazolo[1,5-a]pyridin-2-yl)pyridin-2-ylmethanol;
2-[(3-aminopyrazolo[1,5-a]pyridin-2-yl)hydroxymethyl]-1-methylpyridinium;
2-[(3-aminopyrazolo[1,5-a]pyridin-2-yl)hydroxymethyl]-1-(2-hydroxyethyl)pyridinium;
N-7-(2-imidazo-1-ylpropyl)pyrazolo[1,5-a]pyridine-3,7-diamine;
3-[2-(3-aminopyrazolo[1,5-a]pyridin-7-ylamino)propyl]-1-methyl-3H-imidazol-1-ium;
3-[2-(3-aminopyrazolo[1,5-a]pyridin-7-ylamino)propyl]-1-(2-hydroxyethyl)-3H-imidazol-1-ium;
N-5-(3-imidazo-1-ylpropyl)pyrazolo[1,5-a]pyridine-3,5-diamine;
3-[3-(3-aminopyrazolo[1,5-a]pyridin-5-ylamino)propyl]-1-methyl-3H-imidazol-1-ium;
3-[3-(3-aminopyrazolo[1,5-a]pyridin-5-ylamino)propyl]-1-(2-hydroxyethyl)-3H-imidazol-1-ium;
their acid addition salts; and
their base addition salts.

22. 3-Aminopyrazolo[1,5-a]pyridines according to claim 20, wherein the acid addition salts are chosen from hydrochlorides, hydrobromides, sulfates, citrates, succinates, tartrates, lactates, phosphates, and acetates.

23. 3-Aminopyrazolo[1,5-a]pyridines according to claim 20, wherein the base addition salts are chosen from sodium hydroxide, potassium hydroxide, aqueous ammonia, and amines.

24. A method of dyeing keratinous fibers, comprising:
applying to the keratinous fibers, in an amount effective to dye the fibers, a dyeing composition comprising, in a medium appropriate for dyeing, at least one oxidation base chosen from:
(a) 3-aminopyrazolo[1,5a]pyridines of formula (I), acid addition salts thereof, and base addition salts thereof:

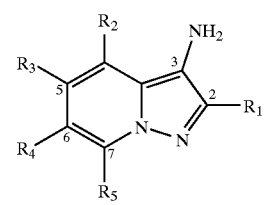

(I)

in which:
$R_1$, $R_2$, $R_3$, $R_4$ and $R_5$ are each independently chosen from: hydrogen; a halogen; an —$NHSO_3H$ radical; a hydroxyl radical; a ($C_1$–$C_4$)alkyl radical; a ($C_1$–$C_4$) alkoxy radical; a ($C_1$–$C_4$)alkylthio radical; a ($C_1$–$C_4$) alkylamino radical; a di($C_1$–$C_4$)alkylamino radical wherein optionally the two alkyl groups, in conjunction with the nitrogen atom to which they are bonded, form a ring optionally interrupted by at least one heteroatom chosen from nitrogen, oxygen and sulfur; a heterocycle; a nitro radical; a phenyl radical; a carbonyl radical; a (($C_1$–$C_4$)alkoxy)carbonyl radical; a carboxamido radical; a cyano radical; an amino radical; a sulfonyl radical; a —$CO_2H$ radical, an —$SO_3H$ radical; a —$PO_3H_2$ radical; a —$PO_4H_2$ radical; and a group of formula (II):

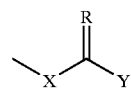

(II)

in which:
R is chosen from oxygen and nitrogen; X is chosen from oxygen, an NH radical, and an NH($C_1$–$C_4$)alkyl radical; and Y is chosen from a hydroxyl radical, an amino radical, a $C_1$–$C_4$ alkyl radical, a ($C_1$–$C_4$)alkoxy radical, a ($C_1$–$C_4$)alkylamino radical, and a di($C_1$–$C_4$)alkylamino radical;

(b) 3-aminopyrazolo[1,5-a]pyridines of formula (Ia), acid addition salts thereof, and base addition salts thereof:

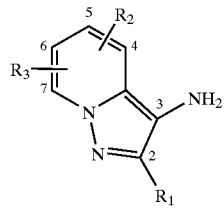

(Ia)

in which:

$R_1$, $R_2$ and $R_3$ are each independently chosen from hydrogen; a halogen; a hydroxyl radical; a ($C_1$–$C_4$) alkyl radical; a ($C_1$–$C_4$)alkylthio radical; a ($C_1$–$C_4$) alkoxy radical; an —NHSO$_3$H radical; an amino radical; a ($C_1$–$C_4$)alkylamino radical; a di($C_1$–$C_4$) alkylamino radical wherein optionally the two alkyl groups, in conjunction with the nitrogen atom to which they are bonded, form a ring optionally interrupted by at least one heteroatom chosen from nitrogen, oxygen and sulfur; a heterocycle; a sulfonamide radical; a carbonyl radical; a (($C_1$–$C_4$)alkoxy)carbonyl radical; a carboxamido radical; and a group of formula (II):

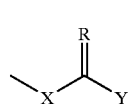

(II)

in which R is chosen from oxygen and nitrogen; X is chosen from oxygen, an NH radical, and an NH($C_1$–$C_4$) alkyl radical; and Y is chosen from a hydroxyl radical, an amino radical, a $C_1$–$C_4$ alkyl radical, a ($C_1$–$C_4$) alkoxy radical, a ($C_1$–$C_4$)alkylamino radical, and a di($C_1$–$C_4$)alkylamino radical; and (c) 3-Aminopyrazolo[1,5-a]pyridines of formula (I'); acid addition salts thereof, and base addition salts thereof:

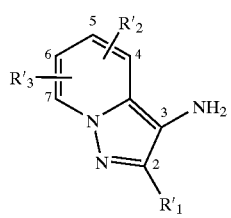

(I')

in which:

R'$_1$ is chosen from: hydrogen; a halogen; a hydroxyl radical; a ($C_1$–$C_4$)alkyl radical; a ($C_1$–$C_4$)alkylthio radical; a ($C_1$–$C_4$)alkoxy radical; an amino radial; a ($C_1$–$C_4$)alkylamino radical; a di($C_1$–$C_4$)alkylamino radical wherein optionally the two alkyl radicals, in conjunction with the nitrogen atom to which they are bonded, form a ring optionally interrupted by at least one heteroatom chosen from nitrogen, oxygen, and sulfur; a heterocycle; and a group of formula (II') below:

(II')

in which:

R' is chosen from oxygen and nitrogen; X' is chosen from oxygen, an NH radical, and an NH($C_1$–$C_4$)alkyl radical; and Y' is chosen from a hydroxyl radical, an amino radical, a $C_1$–$C_4$ alkyl radical, a ($C_1$–$C_4$)alkoxy radical, a ($C_1$–$C_4$)alkylamino radical, and a di($C_1$–$C_4$) alkylamino radical;

R'$_2$ and R'$_3$ are each independently chosen from hydrogen; a halogen; a nitro radical; a heterocycle; an NHSO$_3$H radical; a sulfonamide radical; a ($C_1$–$C_4$) alkyl radical substituted by at least one radical chosen from heterocycles, —CO$_2$H, —SO$_3$H, —PO$_3$H$_2$, —PO$_4$H$_2$, hydroxyl, tri($C_1$–$C_4$)alkylammonium, —NHSO$_3$H, sulfonamide, amino, ($C_1$–$C_4$)alkylamino, a di($C_1$–$C_4$)alkylamino wherein optionally the two alkyl radicals, in conjunction with the nitrogen atom to which they are bonded, form a ring optionally interrupted by at least one heteroatom chosen from nitrogen, sulfur, and oxygen; a ($C_1$–$C_4$)alkylthio radical substituted by at least one radical chosen from hydroxyl, substituted and unsubstituted amino radicals, —CO$_2$H, —SO$_3$H, —PO$_3$H$_2$, and —PO$_4$H$_2$, and a heterocycle; a ($C_1$–$C_4$)alkoxy radical substituted by at least one radical chosen from hydroxyl, substituted and unsubstituted amino radicals, —CO$_2$H, —SO$_3$H, —PO$_3$H$_2$, and —PO$_4$H$_2$, and a heterocycle; an amino radical substituted by at least one ($C_1$–$C_4$)alkyl radical, said at least one alkyl radical optionally substituted by at least one radical chosen from substituted and unsubstituted amino groups, tri($C_1$–$C_4$)alkylammonium, —CO$_2$H, —SO$_3$H, —PO$_3$H$_2$, —PO$_4$H$_2$, —NHSO$_3$H, and a heterocycle;

with the proviso that:

at least one of the radicals R'$_1$ to R'$_3$ is a group other than hydrogen;

the radicals R'$_2$ and R'$_3$ cannot simultaneously be hydrogen;

hen R'$_1$ is a heterocycle, R'$_2$ and R'$_3$ are groups other than a halogen and hydrogen;

when R'$_1$ is hydrogen and when one of the radicals R'$_2$ or R'$_3$ are hydrogen, the other radical R'$_2$ or R'$_3$ is a group other than a hydroxymethyl radical in position 7 or other than a β-hydroxyethyl radical in position 7 or 5;

when R'$_1$ is a methoxy radical and when one of the radicals R'$_2$ or R'$_3$ is hydrogen, the other radical R'$_2$ or R'$_3$ is a group other than chlorine.

* * * * *

UNITED STATES PATENT AND TRADEMARK OFFICE
CERTIFICATE OF CORRECTION

PATENT NO. : 6,730,789 B1
DATED : May 4, 2004
INVENTOR(S) : Véronique Birault, Madelein Laduc and Eric Terranova It is certified that error appears in the above-identified patent and that said Letters Patent is hereby corrected as shown below:

Title page,
Item [57], ABSTRACT,
Line 1, "composition" should read -- compositions --.

Column 17,
Line 45, "3-aminopyrazolo[1,5-a]pyridine-2arboxylic" should read
-- 3-aminopyrazolo[1,5-a]pyridine-2-carboxylic --.

Column 18,
Line 17, "2-methyl-5aminophenol," should read -- 2-methyl-5-aminophenol, --.
Line 42, "oitho-aminophenols," should read -- ortho-aminophenols, --.
Line 65, "3-aminopyrazolo[1,5a]pyridines" should read
-- 3-aminopyrazolo[1,5-a]pyridines --.

Column 19,
Lines 65-66, "3-aminopyrazolo [1,5a]pyridines" should read
-- 3-aminopyrazolo[1,5-a]pyridines --.

Column 22,
Line 30, "3-aminopyrazolo[1,5a]pyridines" should read
-- 3-aminopyrazolo[1,5-a]pyridines --.

Column 24,
Line 52, "hen" should read -- when --.

Signed and Sealed this

Thirtieth Day of November, 2004

JON W. DUDAS
*Director of the United States Patent and Trademark Office*